(12) United States Patent
Penenberg (10) Patent No.: US 8,034,057 B2
(45) Date of Patent: Oct. 11, 2011

(54) APPARATUS FOR, AND METHOD OF, PREPARING FOR AND INSERTING HIP JOINT PROSTHESIS USING COMPUTER GUIDANCE

(76) Inventor: Brad L. Penenberg, Los Angeles, CA (US)

( * ) Notice: Subject to any disclaimer, the term of this patent is extended or adjusted under 35 U.S.C. 154(b) by 2163 days.

(21) Appl. No.: 10/290,770

(22) Filed: Nov. 7, 2002

(65) Prior Publication Data

US 2004/0092944 A1 May 13, 2004

(51) Int. Cl.
*A61F 2/00* (2006.01)
(52) U.S. Cl. ........................................................ 606/91
(58) Field of Classification Search .................... 606/91, 606/86 R, 97, 99, 130; 128/898; 623/22.21–22.39, 623/23.39, 23.4, 23.43
See application file for complete search history.

(56) References Cited

U.S. PATENT DOCUMENTS

| | | | | |
|---|---|---|---|---|
| 4,475,549 A * | 10/1984 | Oh | .................. | 606/91 |
| 4,716,894 A * | 1/1988 | Lazzeri et al. | .................. | 606/91 |
| 4,722,336 A * | 2/1988 | Kim et al. | .................. | 606/130 |
| 4,994,064 A * | 2/1991 | Aboczky | .................. | 606/91 |
| 5,007,936 A * | 4/1991 | Woolson | .................. | 128/898 |
| 5,061,270 A * | 10/1991 | Aboczky | .................. | 606/91 |
| 5,141,512 A * | 8/1992 | Farmer et al. | .................. | 606/87 |
| 5,284,483 A * | 2/1994 | Johnson et al. | .................. | 606/86 |
| 5,320,625 A * | 6/1994 | Bertin | .................. | 606/91 |
| 5,603,318 A * | 2/1997 | Heilbrun et al. | .................. | 600/426 |
| 5,814,050 A * | 9/1998 | Benson | .................. | 606/102 |
| 5,880,976 A * | 3/1999 | DiGioia, III et al. | .................. | 703/7 |
| 5,980,535 A * | 11/1999 | Barnett et al. | .................. | 606/130 |
| 6,224,613 B1 * | 5/2001 | Hofstetter | .................. | 606/130 |
| 6,246,900 B1 * | 6/2001 | Cosman et al. | .................. | 600/426 |
| 6,302,890 B1 * | 10/2001 | Leone, Jr. | .................. | 606/91 |
| 6,351,659 B1 * | 2/2002 | Vilsmeier | .................. | 600/407 |
| 6,395,005 B1 * | 5/2002 | Lovell | .................. | 606/91 |
| 6,694,162 B2 * | 2/2004 | Hartlep | .................. | 600/378 |
| 6,743,235 B2 * | 6/2004 | Subba Rao | .................. | 606/91 |
| 7,535,411 B2 * | 5/2009 | Falco | .................. | 342/174 |
| 2004/0092944 A1 * | 5/2004 | Penenberg | .................. | 606/91 |

OTHER PUBLICATIONS http://www.brainlab.com; Also image from website of Starlock Interface.*

* cited by examiner

*Primary Examiner* — Thomas C. Barrett
*Assistant Examiner* — Christopher Beccia
(74) *Attorney, Agent, or Firm* — Cislo & Thomas LLP; Kelly W. Cunningham, Esq.

(57) ABSTRACT

A cup for a hip replacement is disposed in a first relationship in an operating room with an object providing a sighting for the cup rotation in a first plane. The cup is thereafter rotated in the first plane through a first angle (e.g., 20°-30°). The cup is then disposed in a planar relationship in the operating room with another object providing a sighting for the cup rotation in a second plane transverse (e.g. perpendicular) to the first plane. The cup is subsequently rotated through a second angle (e.g. 40°-45°) in the second plane. In this way, the cup is properly positioned in the acetabulum socket. The length of the leg receiving the hip rotation is then adjusted so that the leg length matches the length of the patient's other leg. This adjustment is provided without affecting the offset position of the center of the ball on the femur.

13 Claims, 6 Drawing Sheets

FIG. 10 the direction of rotation of the cup. An operating table on which the patient is lying may also be used for properly positioning the cup and the direction of rotation of the cup.

APPARATUS FOR, AND METHOD OF, PREPARING FOR AND INSERTING HIP JOINT PROSTHESIS USING COMPUTER GUIDANCE

This invention relates to apparatus for, and a method of, disposing the acetabular and femoral bony surfaces for receiving acetabular and femoral components in a hip replacement for a patient so that the prosthetic components are disposed properly in the hip joint to provide for a stable component relationship when the patient moves his or her leg during daily activities. The invention also relates to apparatus for, and a method of, adjusting the length of a patient's leg receiving a hip replacement so that the length of the leg will match the patient's other leg. The invention further relates to apparatus for, and a method of, adjusting to a preselected value the offset of a patient's leg receiving a hip replacement.

BACKGROUND OF A PREFERRED EMBODIMENT OF THE INVENTION

Great progress has been made in the field of hip replacements. Considering that hip replacements may not have even existed a generation ago, hip replacements are now relatively common in younger as well as older patients. In spite of the considerable progress which has been made, hip replacement instrumentation can be imprecise.

For example, an acetabular component is provided for the femoral head in a patient and for providing for a stable rotational and angular movement of the ball in the socket in accordance with the movements of the patient's leg. The acetabular component includes a cup which has to be disposed in an inclined and horizontally tilted relationship in the patient's pelvis. If the cup is not disposed in a proper relationship to the bony acetabulum, the femoral head will become displaced from the cup (hip dislocation) when the patient moves his or her leg about the cup as a fulcrum. This is often painful and incapacitating and can require the hip replacement operation to be repeated. Since the operation and the subsequent recovery are long, expensive and painful and carry significant medical and surgical risks, a repeat of a hip replacement operation is not to be taken lightly.

Until now, the proper disposition of the acetabular component within the bony acetabulum for a proper rotational movement of the ball and socket joint has been relatively imprecise. In most instances, orthopedic surgeons have held an instrument (holding the cup) for positioning the cup and have judged on an eyeball basis the initial positioning of the instrument and the manual rotation of the instrument in each of two (2) coordinate directions in an attempt to position the cup properly relative to the acetabulum.

More recently, computer guidance in association with preoperative magnetic resonance imaging (MRI and computed tomography (CT), and/or x-ray techniques have been employed to assist in determining the coordinates through which the cup has had to be moved to be oriented in a proper relationship to the pelvis. Such techniques have been costly and labor intensive, particularly since the determinations made as by magnetic resonance techniques have had to be registered in the operating room by time consuming point Verification to connect the operative bony anatomy to the pre-operative image data. The application of these techniques by using such imaging studies in the operating room have added substantial time and cost to the operative procedure and have raised a question as to the true value of such techniques. As a result, any initial advantage provided by such techniques such as the magnetic resonance imaging or computed tomography outside of the operating room have been nullified.

As a result of the imprecise instrumentation now being provided to position a cup and femoral component properly relative to the pelvis and bony acetabulum and femur, approximately 2 to 10% of hip replacement operations have suffered the complication of dislocation as a result of component malpositioning. Considering that hip replacement operations are painful and expensive and the recovery can be lengthy and painful, full recovery from a hip replacement operation usually requires months until the recovery can be considered to be at all complete. Rigid exercise schedules during the period of recovery have often had to be imposed.

In a hip replacement operation, certain trial components are utilized prior to placing the actual prosthesis. For example, the ball (femoral head) disposed at the top of the femur and providing the rotational relationship with the socket in the acetabulum is replaced by a metal ball. Furthermore, a liner made from a suitable plastic having low frictional characteristics is disposed on the acetabulum to receive the metal ball. These removals, replacements and insertions affect the length of the patient's leg receiving the hip replacement. If the length of this leg does not match the length of the patient's other leg, the patient will walk with a limp. Techniques to match the length of the leg receiving the hip replacement to the length of the other leg have not been entirely satisfactory.

When attempts have been made to match the length of the patient's leg receiving the hip replacement to the length of the patient's other leg, the position of the center of the cup has become offset from its optimum position. This can affect the ability of the femur ball to rotate in the acetabulum socket and can also affect the ease with which the rotation occurs. This problem has not been satisfactorily addressed in the prior art.

BRIEF DESCRIPTION OF PREFERRED EMBODIMENTS OF THE INVENTION

A cup attached to the acetabulum for a hip replacement is disposed in a first relationship with one of the objects in an operating room where the object provides a sighting for the cup rotation in a first plane. The object may be a line of tiles on a vertical wall in the operating room or may be a pole supported on the floor of the operating room for holding intravenous fluid for introduction into the patient. The cup is thereafter rotated in the first plane through a first angle. The plane may be a horizontal plane and the angle may be approximately 20-30°.

The cup is then disposed in a planar relationship with one of the objects in the operating room where the object provides a sighting for the cup rotation in a second plane transverse (e.g. substantially perpendicular) to the first plane. The object may be an operating table on which the patient is lying and the second plane may be vertical and the angle may be approximately 40°-45°. The cup is subsequently rotated through the second plane. The acetabular component is then disposed for functional rotation relative to the femoral component in accordance with the movement of the patient's leg about the cup as a fulcrum.

The system and method of this invention provide certain advantages. They provide an accurate disposition of the cup in horizontal and vertical directions by using as accessories objects commonly existing in all operating rooms. For example, a line of tiles on a wall in the operating room or a pole for holding containers for an intravenous fluid to be applied to the patient during the hip replacement may provide a vertical reference for properly positioning the cup and the edges of the operating table may serve as a horizontal reference. These accessories in the operating room provide for an accurate and reliable disposition of the cup in the horizontal and vertical directions with a minimal expense and a minimal expenditure of time. This is important because the disposition of the cup in the horizontal and vertical directions occurs after the patient has been cut and is bleeding. The utility and operation of this invention therefore provide for a reduced loss of blood and overall less risk to the patient.

Rather than using preoperative imaging data as a reference for acetabular or femoral component positioning, intraoperative referencing is established based on certain assumptions regarding the pelvic bone position on the operating table in reference to the operating table and the walls and floor of the operating room. With regard to the femur, the neutral axis is set based on setting an intramedullary awl in line with the lateral aspect of the medial femoral condyle and the anteversion is set in reference to the horizon and the leg below the knee is perpendicular to the operating table. The pelvis is secured either with the patient supine or in the side lying (decubitus) position. This sets the reference plane of the bony pelvis and the bony acetabulum in a reliable relationship to the level plane of the operating table and the wall and corners of the operating room. The zero position is then set (registered) with a computer and any angular movement is measured by displacement of the transmitters attached to the instrumentation guides from this zero position.

The system and method of this invention also provide for an adjustment in the length of the patient's leg receiving the hip replacement so that this length matches the length of the patient's other leg. In this way, the patient is able to walk without a limp after his or her recovery from the hip replacement. The system and method of this invention also provide for an adjustment in the offset of the patient's leg receiving the hip replacement so that there is no offset of the patient's leg from what is considered to be an optimal value.

DETAILED DESCRIPTION OF PREFERRED EMBODIMENTS OF THE INVENTION

Figure 1:
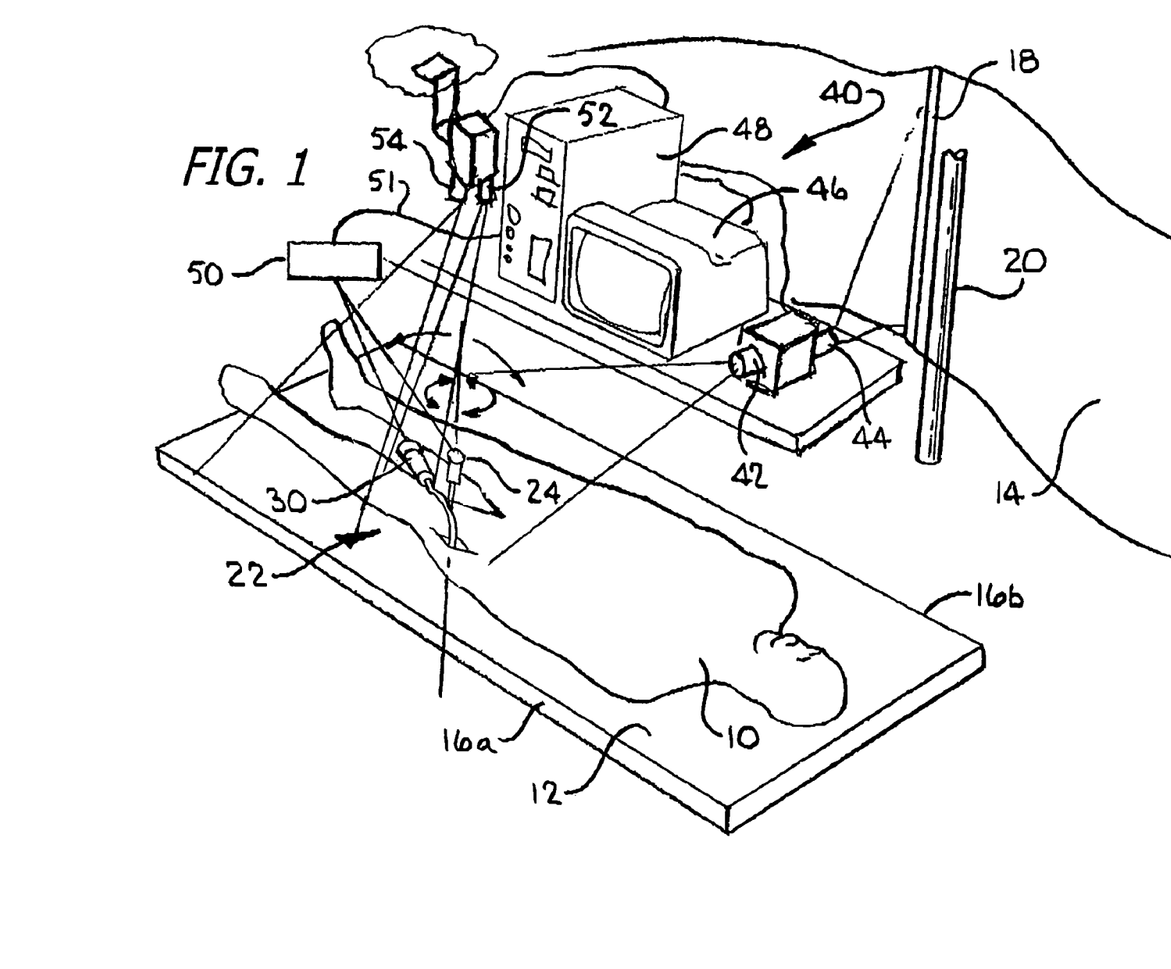
FIG. 1 is a schematic perspective view of a patient on an operating table in an operating room as seen from a position above, in front of and to one side of the operating table and shows an instrument, including a cup on the instrument, and equipment for positioning the cup to provide an optimal relationship with an acetabulum.

FIG. 1 is a schematic perspective view of a patient 10 lying on an operating table 12 in an operating room 14. The periphery of the operating table may be defined by a pair of spaced and substantially parallel longitudinal edges 16a and 16b each having a substantially linear disposition. A vertically disposed slat or tiles 18 may be disposed on one of the walls of the operating room 14. A vertically disposed pole 20 may be provided in the operating room 14 to hold a container of an intravenous fluid for insertion into the patient during the hip operation.

An instrument generally indicated at 22 is shown in FIG. 1 as being disposed in the hip of the patient. The instrument 22 is known in the prior art but not in combination with the apparatus included in this invention. The instrument 22 is also shown on an enlarged and detailed basis in FIG. 3. The instrument 22 includes a handle portion 24 and a stem 26 integrally joined to the handle portion as at 28. The handle portion 24 and the stem 26 are preferably disposed in the same plane. The stem 26 extends upwardly in a curved configuration from the joined position 28 and has a sleeve 30 at its upper end. The stem 26 also extends downwardly in a curved configuration from the juncture 28 and has a cup 34 (FIGS. 3 and 9) at its lower end. The cup 34 may constitute a hollow hemisphere which is made from a suitable material such as a low friction plastic and which is disposed in a socket in the patient's acetabulum 36 to provide for rotary movements of a ball 33 at the upper end of a femur 35 in the acetabulum socket in accordance with movements of the patient such as occurs in walking or running.

In order to insure that rotation will occur freely between the cup 34 and the ball 33 on the femur 35 (FIG. 9) while the patient is running or walking, the cup has to be positioned properly relative to the ball. This proper positioning of the acetabulum cup 34 relative to the acetabulum 36 involves an initial positioning of the cup in the plane defined by the stem 26 and the handle portion 24. This initial positioning of the cup 34 is indicated schematically in FIG. 3 and is indicated by an arrow 37 in FIG. 3.

Thereafter the cup 34 is rotated to a position in which it is tilted upwardly (see arrow 37 in FIG. 3) in the plane of the paper through an angle between approximately 40° and 45° and in which it is tilted horizontally into the plane of the paper through an angle of between approximately 20° and 30°. This horizontal tilting is indicated by an arrow 39. After such rotations, the cup 34 is aligned with the acetabulum 36 so that the ball is properly positioned in the socket in the acetabulum.

Instrumentation generally indicated at 40 (FIG. 1) is provided to position the cup 34 properly relative to the acetabulum 36. The instrumentation includes a pair of cameras 42 and 44. The camera 42 is directed toward the handle 24 and the camera 44 is directed toward the slat or tile 18 or the vertically disposed pole 20. The cameras 42 and 44 indicate whether the handle portion 24 is vertically aligned with the slat or tile 18 or the pole 20. This may be indicated on a display monitor 46 and may also be indicated in a data processor 48.

The data processor 48 may be operative to adjust the positioning of the handle portion 24 in the vertical direction so that the handle portion becomes vertically aligned with the slat or tile 18 or the pole 20. The movement of the handle portion 24 to the vertical position may be provided by a mechanism 50 in accordance with input signals introduced to the mechanism from the data processor 48. Although the mechanism 50 is indicated only schematically, it is believed that a person of ordinary skill in the art will know how to build, without any significant experimentation, and move the instrument 22 to a vertical disposition. The coupling between the mechanism 50 and the data processor 48 is indicated schematically by a line 51 in FIG. 1. The instrument 22 is then rotated in a horizontal plane through an angle between approximately 20° and 30° about the cup as a fulcrum.

In a similar manner, cameras 52 and 54 are included in the instrumentation 40. The camera 52 is directed toward the instrument 22 and the camera 54 is directed toward the longitudinal edge 16a of the operating table 12. The cameras 52 and 54 sense whether the stem 26 is parallel to the longitudinal edge 16a of the table 12 as seen from a position above the patient 10 and the instrument 22. The signals from the cameras 52 and 54 are introduced to the data processor 48 which operates upon the mechanism 50 to adjust the positioning of the stem 26 so that the downward projection of the stem on the operating table 12 is substantially parallel to the longitudinal edge 16a of the operating table 12. The mechanism 50 then operates, under the control of the data processor 48, to rotate the cup in a substantially vertical plane about the cup 34 as a fulcrum through an angle between approximately 40° and 45°. The construction and the operation of the mechanism 50 under the control of the data processor 48 are believed to be obvious to a person of ordinary skill in the art.

Figures 2, 3:
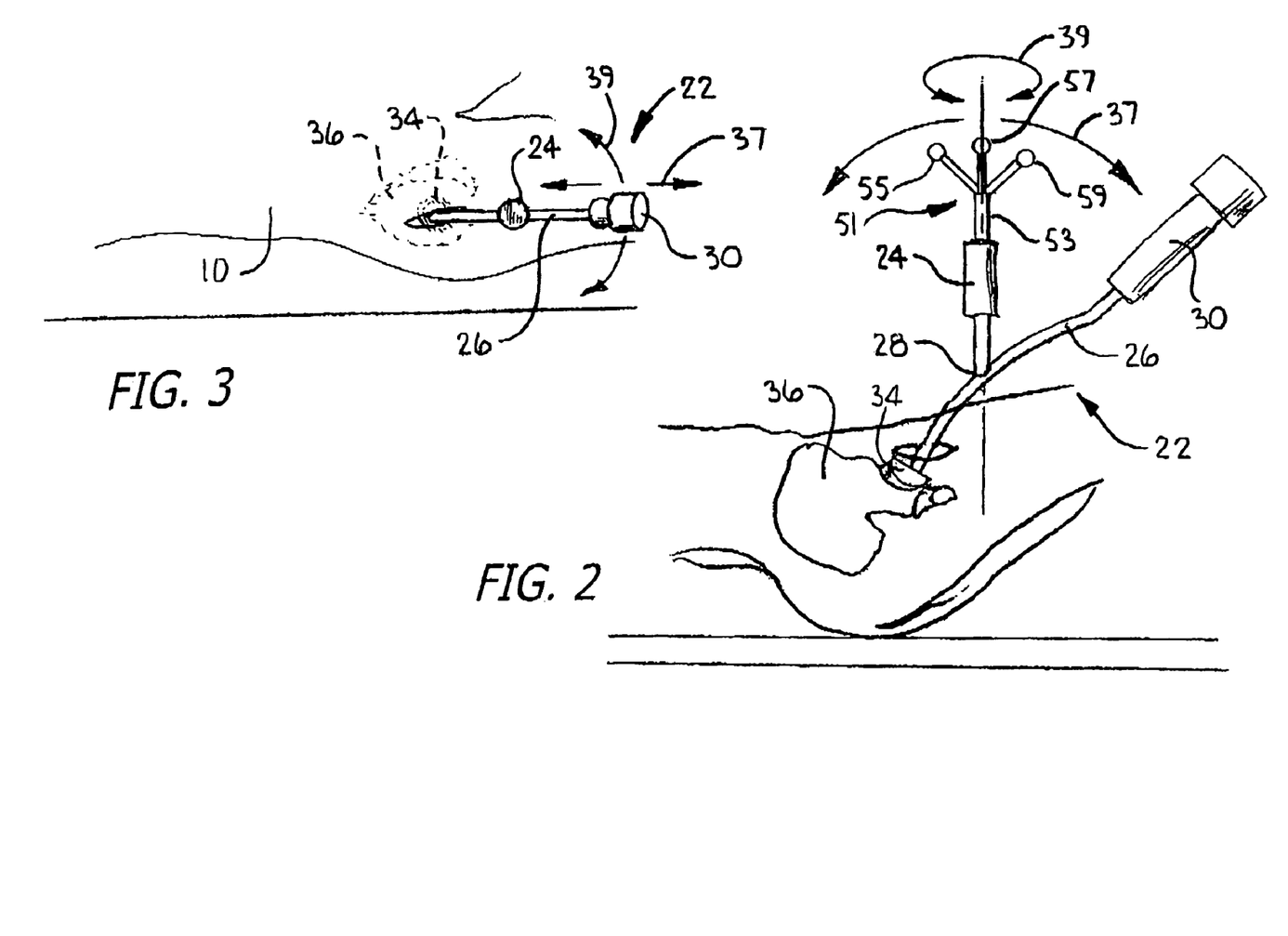
FIG. 2 is an enlarged schematic front elevational view of the instrument shown in FIG. 1 and shows the instrument in a position relative to the pelvic region of the patient to provide for a movement of the cup in horizontal and vertical planes to a position for receiving the patient's acetabulum.
FIG. 3 is a schematic top plan view of the instrument and shows the pivotal movement of the cup in the vertical plane.
Figure 4:
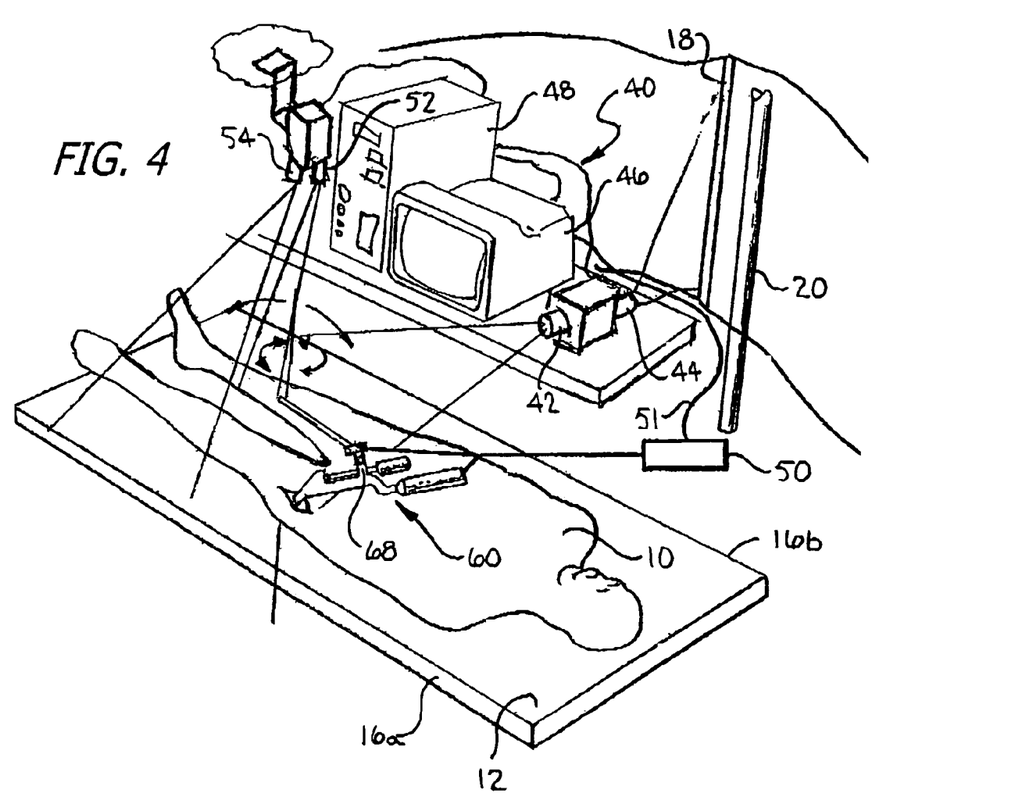
FIG. 4 is a schematic perspective view similar to that shown in FIG. 1 but showing a different instrument than that shown in FIG. 1.

A positioning device generally indicated at 51 in FIG. 2 may extend upwardly in FIG. 2 from the handle portion 24. The positioning device 51 is an addition to the instrument 40 which is known in the prior art. It includes a shaft 53 and transmitters 55, 57 and 59. The positioning device 51 has been provided by BrainLab of Munich, Germany and has been designated by PorainLab by VectorVision. The positioning device 51 has been provided in the prior art but not for the purposes of this invention. The transmitters 55, 57 and 59 are separated from each other in a direction substantially perpendicular to the direction of the handle portion 24. The transmitters 55, 57 and 59 cooperate with the microprocessor 48 in tracking the positioning of the cup 34 and in providing a rotary movement of the cup to the proper angular positions in the two (2) coordinate directions.

It will be apparent to a person of ordinary skill in the art that other mechanisms than that shown in FIGS. 1-3 and described above may be used, without departing from the scope of the invention, to position the instrument 22 so that the cup 34 is disposed in the proper position relative to the acetabulum 36. For example, instead of using cameras, electron beams may be used to properly position the handle portion 24 in the vertical direction relative to the slat or tiles 18 or the pole 20 and to properly position the stem 26 properly relative to the horizontal edge 16a of the operating table 12.

Another embodiment of instrument action is generally indicated at 60 in FIGS. 4-7. The instrument 60 (FIG. 7) may be obtained as a commercial item from Zimmer, Inc. The instrument 60 includes a handle portion 62 and a holding portion 64 which extends from the handle portion in the same general direction as the handle portion. A cup 66 corresponding to the cup 34 is disposed at the end of the holding portion 64. A support portion 68 extends integrally from the holding portion 64 in a direction transverse (preferably substantially perpendicular) to the holding portion.

Figure 7:
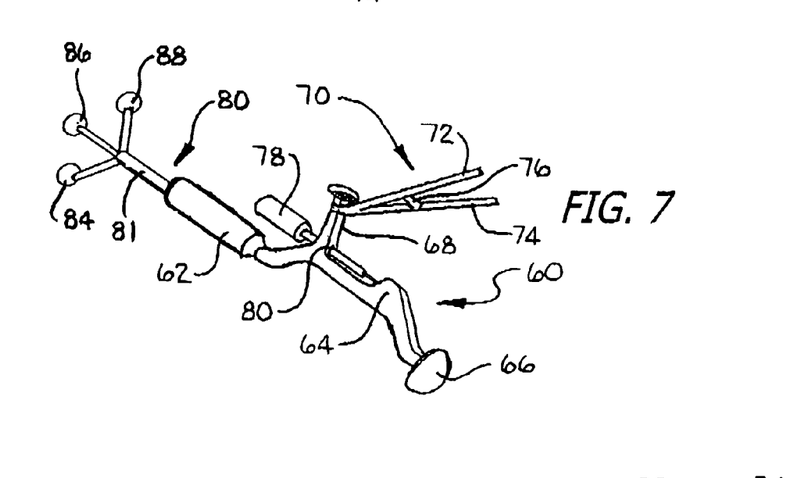
FIG. 7 is an enlarged schematic perspective view of the instrument shown in FIG. 4 as seen from a position above and in front, and to the right, of the instrument.

An A-frame structure generally indicated at 70 extends from the support structure 68 substantially horizontally in a direction substantially perpendicular to the support structure. The A-frame structure includes a pair of spaced arms 72 and 74 and a bar 76 disposed between the arms at an intermediate position along the lengths of the arms to rigidify the positioning of the arms relative to each other. The angle between the arms 72 and 74 may be any suitable angle between approximately 20° and 30°. A member 78 extends through an opening 80 in the support structure 68.

Figure 5:
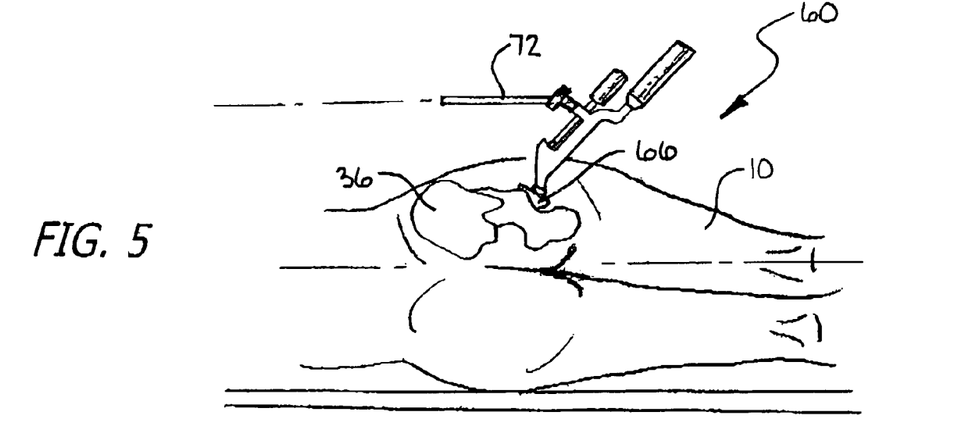
FIG. 5 is a front elevational view of the instrument when disposed in the pelvic region of the patient.
Figure 6:
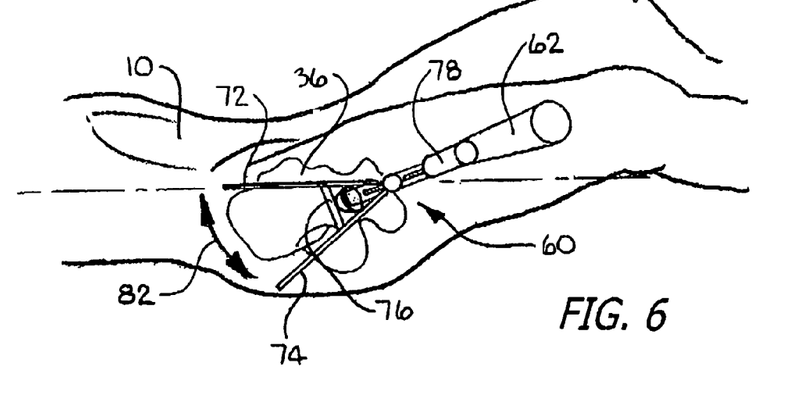
FIG. 6 is a top plan view of the instrument when disposed in the pelvic region of the patient with the patient lying on his or her back.

FIGS. 5 and 6 show how the instrument 60 is used to position the cup 66 properly relative to the ball 33 in the femur 35. FIG. 6 is a top plan view with the patient 10 lying on his or her back and with the instrument 60 disposed in the pelvic region of the patient's body. As a first step, the support portion 68 is aligned vertically with the slat or tiles 18 or the pole 20. The instrument is then rotated in a horizontal plane about the cup as a fulcrum through an angle between approximately 20° and 30° while the support portion is maintained in parallel relationship to the slat or tiles 18 or the pole 20. The angle between approximately 20° and 30° corresponds to the angle between the arms 72 and 74. In other words, the rotation causes one of the arms 72 and 74 to be disposed at the position where the other one of the arms has been previously disposed when the rotation has been initiated. The rotary movement of the instrument 60 in a horizontal plane about the cup 66 as a fulcrum is indicated by an arrow 82 in FIG. 6.

FIG. 5 is a front elevational view of the patient 10 and the instrument 60. In this relationship, the arm 72 is moved to a position in which it is parallel to the longitudinal edge 16a of the operating table 12 when viewed from a position above the instrument 60 and the patient 10. The instrument 60 is then rotated in a vertical plane about the cup 66 as a fulcrum through an angle between approximately 40° to 45° while maintaining the arm 72 substantially parallel to the longitudinal edge 16a of the operating table when viewed from a position above the instrument and the patient. In providing this rotation, the cameras 42 and 44 may be disposed in positions corresponding to the positions of these cameras in FIG. 1.

A positioning device generally indicated at 80 in FIG. 7 may extend from the handle portion 62 in FIG. 7. The positioning device 80 may have a construction corresponding to the positioning device 51 in FIG. 2. The positioning device 80 may include a handle 81 and transmitters 84, 86 and 88 displaced from one another in a direction substantially perpendicular to the handle portion 62. The transmitters 84, 86 and 88 cooperate with the microprocessor 48 in tracking the position of the cup 66 and in providing a rotary movement of the cup to the proper angular positions in the two (2) coordinate directions.

Figure 8:
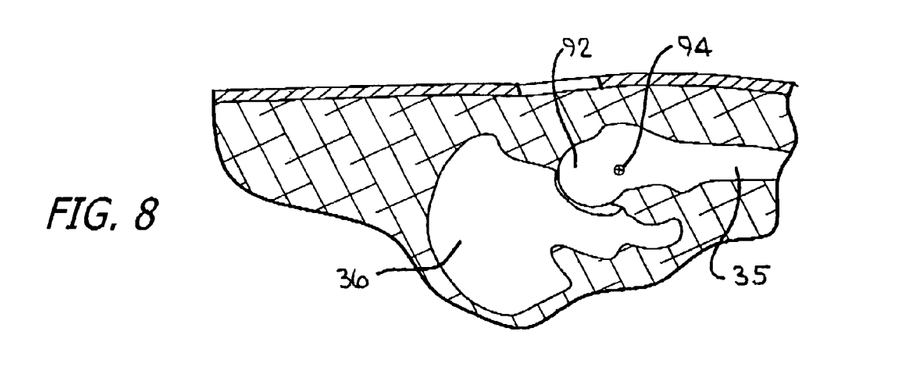
FIG. 8 is a fragmentary schematic sectional view showing an acetabulum in an operative relationship with a femur for providing a rotational relationship between the acetabulum and the femur to provide a proper operation of the hip in producing locomotion of the patient.

FIG. 8 shows the acetabulum 36, the femur 35, and the femoral head 92 of the femur in an operatively coupled relationship to each other. The acetabulum may hold the cup 34 to provide for the rotary movement of the ball 33 in the cup. The femur is rotatable in the cup 34 in the acetabulum 36 when the patient walks or runs. A pin 94 may be disposed on the femur 35 to provide for an adjustment in the length of the femur so as to provide the femur in the hip being replaced with the same length as the femur in the other leg. In this way, the patient will walk evenly without a limp after recovery from the hip replacement. The disposition of a pin such as the pin 94 on the femur 35 is known in the prior art.

Figures 9, 11A, 11B:
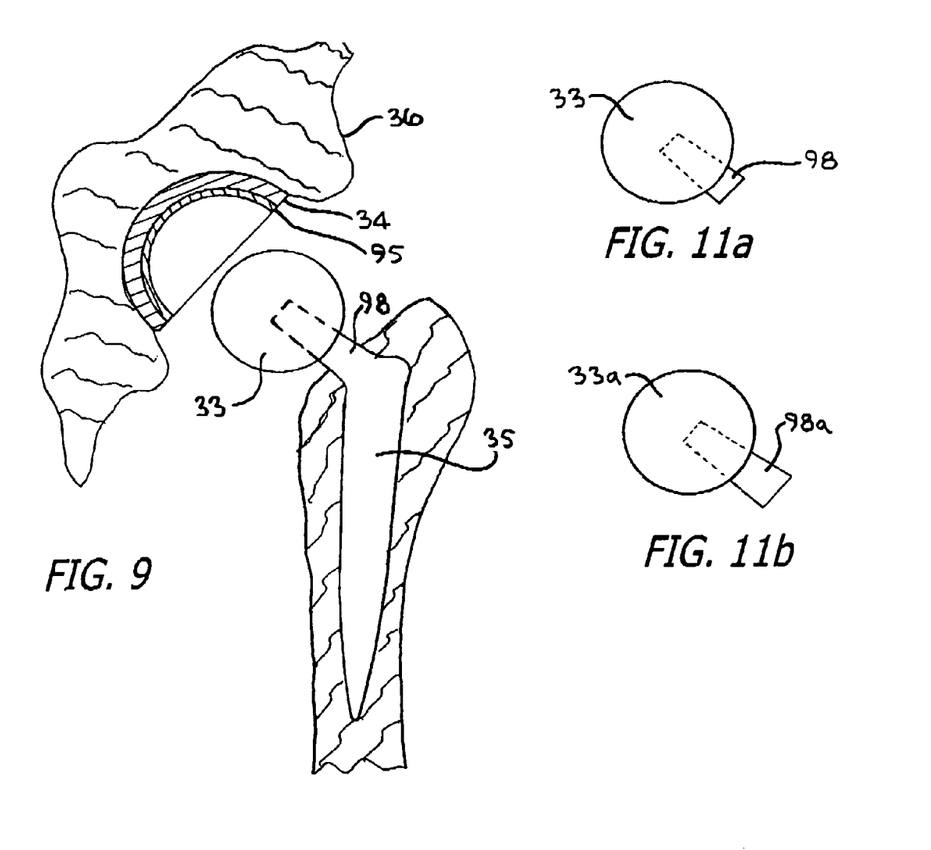
FIG. 9 is a fragmentary sectional view showing the replacement of, and the addition to, certain portions of the acetabulum and the femur during a hip replacement operation.
FIGS. 11a and 11b schematically show how the length of the patient's leg receiving the hip replacement can be adjusted by varying the length of certain components added to the femur during the hip replacement operation to substitute for corresponding components previously in the patient's femur.

FIG. 9 is an enlarged fragmentary schematic view of the relationship between the femur 35 and the acetabulum 36 when a hip replacement has been provided in the leg of a patient. As will be seen, the cup 34 is attached to the acetabulum 36 and may be made from a suitable material such as a metal. The cup 34 may be considered as a liner for the acetabulum 36. The cup 34 may have a hollow hemispherical shape. An insert 95 made from a suitable plastic material such as a plastic having a low friction (e.g. ultra high molecular weight polyethylene) is attached to the cup 34. The insert 95 has a hollow hemispherical shape corresponding to the shape of the cup 34. The spherical ball 33 made from a suitable material such as a metal is disposed within the insert 95 for rotation relative to the insert when the patient walks or runs. The ball 33 has an extension 98 which is suitably attached to the upper end of the femur 35.

The pin 94 is provided to match the length of the patient's leg receiving the hip replacement to the length of the patient's other leg. The pin 94 is shown in additional detail in FIG. 10. It is provided with external threads to facilitate insertion of the pin 94 into the femur 35 of the patient's leg receiving the hip replacement. The pin 94 is hollow so that it can receive and hold a shaft 100 which supports a plurality of transmitters 102, 104 and 106 each of which may be constructed in a similar manner. The transmitters 102, 104 and 106 are displaced from each other in the direction of the length of the femur 35.

Figure 10:
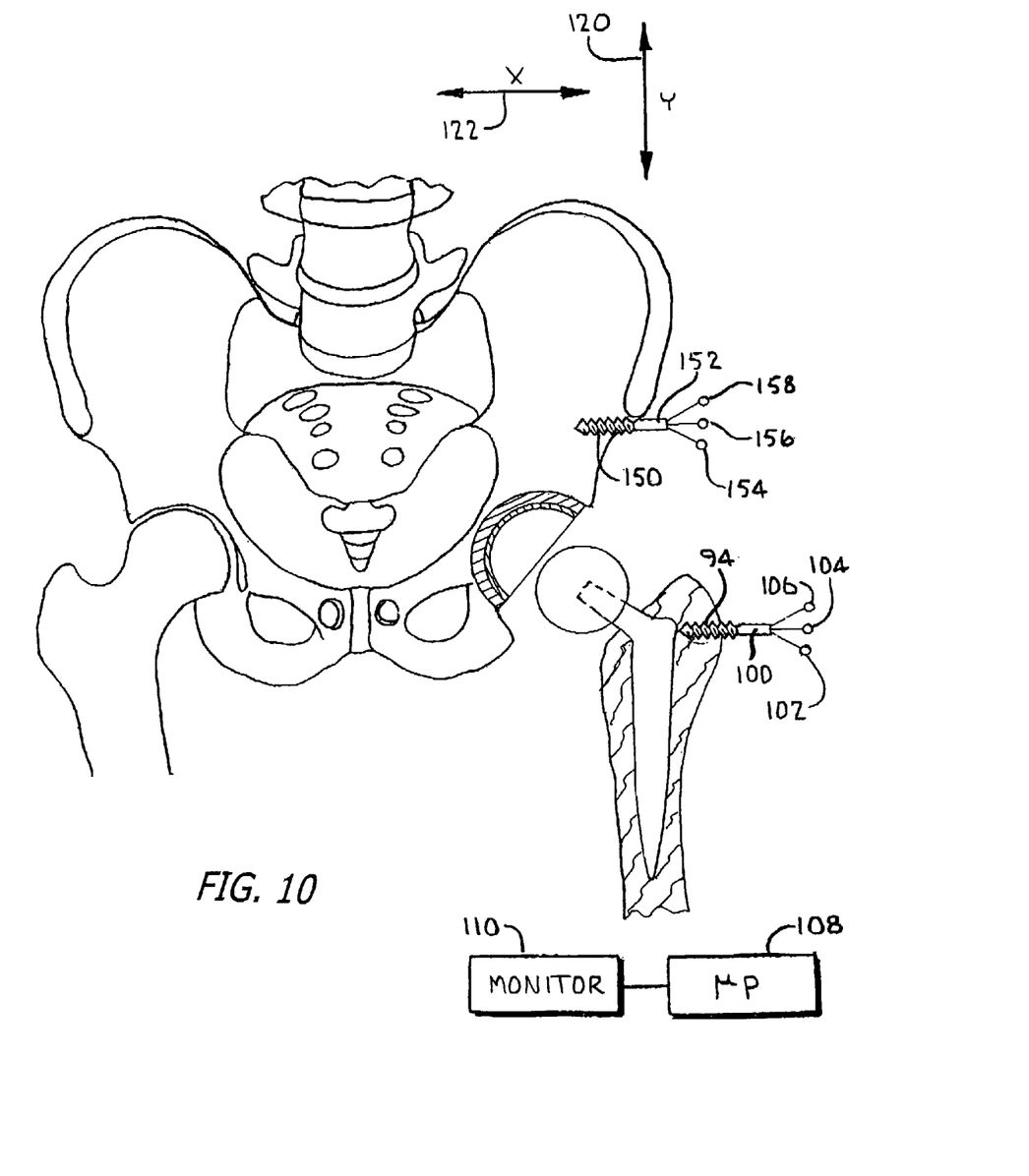
FIG. 10 is a schematic view, partly in section and partly in block form, showing a system for adjusting the length of the patient's leg receiving the hip replacement so that the length of this leg matches the length of the patient's other leg.

The transmitters 102, 104 and 106 are included in equipment designated as Vector Vision by BrainLab of Munich, Germany. The equipment includes a microprocessor 108 and a vision monitor 110. Similar equipment may be obtained from Medtronics. The Vector Vision equipment has provided positional measurements in the prior art but is not believed to have provided for a patient's leg receiving a hip replacement to have the same length as the patient's other leg.

The transmitters 102, 104 and 106 simultaneously or sequentially transmit signals to the microprocessor 108. The microprocessor 108 has been preset to provide an output signal having particular characteristics when the pin 94 is at a position where the length of the patient's leg receiving the hip replacement matches the length of the patient's other leg. The microprocessor 108 processes the signals from the transmitters 102, 104 and 106 to determine the characteristics of the output signal. Dependent upon the characteristics of the output signal, the microprocessor 108 determines and indicates whether the patient's leg receiving the hip replacement has the same length as, or is shorter or longer than, the patient's other leg.

Assume that the length of the patient's leg receiving the hip replacement is less than the proper length. The ball 33 and the extension 98 previously provided for the hip replacement can be replaced by another ball 33a and another extension 98a as in FIG. 11. The replacement ball 33a can have the same dimensions as the replaced ball 33. However, the extension 98a in the replacement unit can have a greater length than the length of the extension 98 previously provided for the hip replacement. In this way, the effective length of the patient's leg receiving the hip replacement can be adjusted to have the length of this leg match the length of the patient's other leg.

As will be appreciated, different lengths for the extension 98 affect the length of the leg receiving the hip replacement. The different lengths of the extension 98 also affect the offset of the center of the ball from the pin 94 in a direction substantially perpendicular to the direction of the length of the leg. The direction corresponding to the length of the leg is indicated by an arrow 120 in FIG. 10 and the direction of the offset is indicated by an arrow 122 in FIG. 16. It is desirable for the offset to be substantially constant even as the length of the extension 98 is adjusted to make the length of the leg receiving the hip replacement equal to the length of the other leg.

A pin 150 is attached to the patient's pelvis. The pin 150 is hollow. A shaft 152 is disposed in the pin 150. The shaft holds transmitters 154, 156 and 158 which are displaced from one another in the direction of the length of the femur. The transmitters 154, 156 and 158 transmit to the microprocessor 108 signals which indicate the movements of the patient's body. The microprocessor 108 operates to eliminate the effect of the movement of the patient's body so that only the deviation of the pin 94 from the desired position as a result of a change in the length of the patient's leg is indicated by the microprocessor.

Figure 12A:
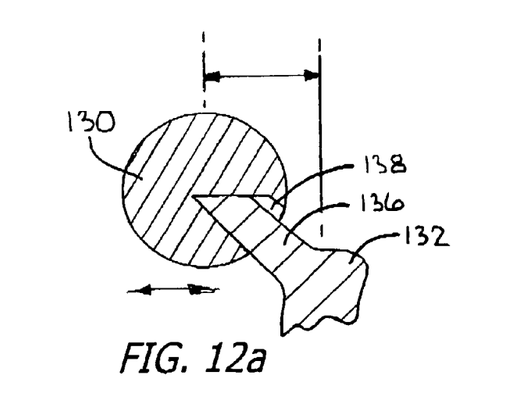
FIGS. 12a and 12b schematically show how any offset in the center of the rotary ball at the upper end of the femur can be adjusted so that the center of the ball does not become offset during the hip replacement operation.
Figure 12B:
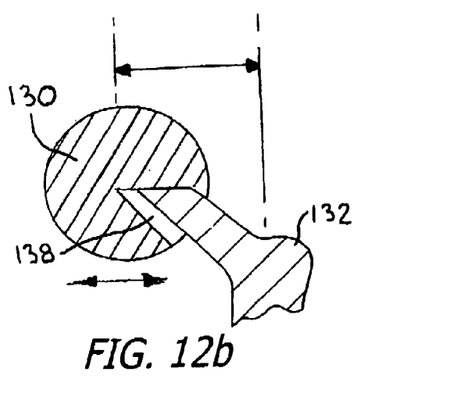

FIGS. 12a and 12b are schematic representations of one way of maintaining the offset between the pin 94 and the center of the cup 34 substantially constant. In FIGS. 12a and 12b, a hollow ball 130 and an extension 132 are provided. The total length of the ball 130 and the extension 132 in the direction of the arrow 120 in FIG. 10 is a known constant. An insert 136 is disposed in the ball 130 and is movable in the ball with the extension 132. This may be seen from a comparison between the position of the insert 136 and the extension 132 in FIGS. 12a and 12b relative to the ball 130.

The insert 136 and the extension 132 are attached to the femur 35. The insert 132 is movable in a cut-out 138 in the ball 130 in the axial direction to maintain the distance between the center of the ball and the pin 94 substantially constant even when the effective length of the extension 98 is changed as shown in FIGS. 10a and 10b. This may be seen from FIGS. 12a and 12b. In FIG. 12a, the insert 136 is shown at the left end of the cut-out 138 and in FIG. 12b the insert is shown at the right end of the cut-out. In this way, the offset is changed without changing the length of the patient's leg receiving the hip replacement.

It will be appreciated that the insert 136 in FIGS. 12a and 12b may actually be equivalent to the extension 98 in FIGS. 10a and 10b. Any empty space in the disposition of extension 98 within the ball 33 in FIGS. 10a and 10b and in the cut-out 134 in FIGS. 12a and 12b may be filled with bone fragments and cement in a manner corresponding to the manner in which bone fragments and cement fill the femur 35 in methods now used in hip replacement prostheses.

As will be seen, the insert 136 is movable axially in the hollow ball 132 and the hollow extension 132 between the positions shown in FIGS. 12a and 12b. This does not affect the position of the center of the ball 130 in the direction of the length of the patient's leg receiving the hip replacement since the position of the ball is constant in that direction even with the axial movements of the insert 136. However, the movement of the insert 136 in the offset direction in the ball 130 and the extension 132 affects the offset position of the ball 130. This provides for an adjustment in the offset of the center of the ball 33 so as to maintain the offset position of the center of the ball substantially constant.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. A method of disposing a cup in a socket in an acetabulum in an operating room, for a hip replacement, including the steps of:
disposing the cup in a first particular relationship to a first object in the room other than an axis of a patient or a cup positioning instrument, wherein the first object is a selected one of a wall member of the operating room or a pole for supporting medical equipment in the operating room that defines a vertical line in a particular direction in the operating room,
thereafter rotating the cup through a first particular angle in a first direction about the cup as a fulcrum in accordance with the first particular relationship,
subsequently disposing the cup in a second particular relationship to a second object in the room other than an axis of a patient or a cup positioning instrument, wherein the second object is an edge of an operating table defining a horizontal line in a particular direction in the operating room,
said first and second objects remaining stationary during the method to thereby provide a pair of fixed references, and
rotating the cup through a second particular angle in a direction transverse to the first direction about the cup as a fulcrum in accordance with the second particular relationship.

2. A method as set forth in claim 1 wherein the cup is rotated through the first particular angle in a plane substantially perpendicular to the first perpendicular relationship to the first object in the room.

3. A method as set forth in claim 1 wherein the cup is disposed in a substantially parallel relationship to the second object in the operating room where the second object is transverse to the first object.

4. A method as set forth in claim 3 wherein the cup is rotating substantially horizontally through the first particular angle about the cup as a fulcrum relative to the first object and wherein the cup is rotated substantially vertically through the second particular angle about the cup as a fulcrum relative to the second object.

5. A method as set forth in claim 4 wherein the cup is disposed in a socket in the acetabulum after the rotation of the cup through the first and second angles.

6. A method as set forth in claim 2 wherein the first angle of rotation is between approximately 20° and 30°.

7. A method as set forth in claim 4 wherein the first particular angle is between approximately 20° and 30° and wherein the second particular angle is approximately 40° to approximately 45°.

8. A method set forth in claim 1 wherein the cup is rotated through the first particular angle about the cup as a fulcrum in a plane substantially perpendicular to the first object in the operating room and wherein the cup is disposed in a second substantially parallel relationship to the second object in the operating room and wherein the cup is disposed in a socket in the acetabulum after the rotation of the cup through the first and second angles and wherein the first angle of rotation is between approximately 20° and 30° and wherein the second particular angle is approximately 40° to approximately 45°.

9. A method of disposing a cup in a socket in an acetabulum in an operating room, for a hip replacement, including the steps of:
aligning a first member on an instrument with a first physical reference in the operating room other than an axis of a patient or a cup positioning instrument,
rotating the instrument through a first particular angle about the cup as a fulcrum in a first direction defined by the first member,
aligning a second member on the instrument with a second physical reference in the operating room other than an axis of a patient or a cup positioning instrument,
said first and second objects remaining stationary during the method to thereby provide a pair of fixed references,
the second physical reference having a particular dispositional relationship with the first member, and
rotating the instrument, in a second direction coordinate with the rotation of the instrument in the first direction; through a second particular angle about the cup as a fulcrum,
wherein a cup is disposed on the instrument for movement with the instrument through the first and second particular angles about the cup as a fulcrum, and
wherein the first member in the operating room has a vertical disposition relative to a wall in the operating room to provide for a rotation of the instrument in the first direction in a plane defined by the first member and wherein the second member in the instrument has a horizontal disposition relative to an article in the room to provide for a rotation of the instrument in the second direction in a plane defined by the second member and wherein the first angle of rotation of the instrument in the first direction is between approximately 20° and 30° and wherein the second angle of rotation of the instrument in the second direction is between approximately 40° and 45° and wherein the first direction is defined by a selected one of a vertical slat or tile on the wall of the operating room or an instrument pole for supporting medical equipment in the operating room in the operating room and the rotation of the instrument in the first direction is about the cup as a fulcrum and wherein the second direction is defined by one of the edges of an operating table in the room and the rotation of the instrument in the second direction is about the cup as a fulcrum.

10. A method of disposing a cup in a socket in an acetabulum in an operating room for a hip replacement, including the steps of:
disposing the cup in a first particular relationship with a first one of the objects in the operating room other than an axis of a patient or a cup positioning instrument where the first object provides a sighting for a rotation of the cup in a first planar direction and is a selected one of a wall member of the operating room or a pole for supporting medical equipment in the operating room that defines a vertical line in a particular direction in the operating room,
thereafter rotating the cup about the cup as a fulcrum through a first particular angle in a direction defined by the first particular relationship,
disposing the cup in a planar relationship with a second one of the objects in the operating room other than an axis of a patient or a cup positioning instrument where the second object provides a sighting for a rotation of the cup in a second planar direction transverse to the first planar direction,
said first and second objects remaining stationary during the method to thereby provide a pair of fixed references, and thereafter rotating the cup about the cup as a fulcrum through a second particular angle in the second planar direction, wherein the first object providing the first particular relationship with the cup in the operating room has a vertical disposition to provide for a rotation of the cup in a horizontal plane through the first particular angle and wherein the second object providing the second particular relationship with the cup in the operating room has a horizontal disposition to provide for a rotation of the cup in a vertical plane through the second particular angle, and wherein the second planar direction is substantially perpendicular to the first planar direction and wherein the cup is disposed in a socket in the acetabulum for a rotation of a ball in a femur relative to the cup after the cup has been rotated in the first planar direction about the cup as a fulcrum through the first particular angle and has been rotated in the second planar direction about the cup as a fulcrum through the second particular angle and wherein the first object providing the first particular relationship with the cup in the operating room has a vertical disposition to provide for a rotation of the cup in a horizontal plane about the cup as a fulcrum through the first particular angle and wherein the second object providing the disposition of second particular relationship with the cup in the operating room has a horizontal disposition to provide for a rotation of the cup in a vertical plane about the cup as a fulcrum through the second particular angle.

11. A method of disposing a cup in a socket in an acetabulum in an operating room for a hip replacement, including the steps of:

providing an instrument for holding the cup, the instrument including a first portion for alignment vertically relative to a first object in the operating room other than an axis of a patient or a cup positioning instrument and including a second portion for alignment horizontally relative to a second object in the operating room other than an axis of a patient or a cup positioning instrument, said first and second objects remaining stationary during the method to thereby provide a pair of fixed references, aligning the first portion of the instrument vertically relative to the first object in the operating room, rotating the cup horizontally through a first particular angle, aligning the second portion of the instrument horizontally relative to the second object in the operating room, and rotating the cup vertically through a second particular angle, and wherein the first object is selected from a group consisting of a slat or tile on the wall of the operating room or an instrument pole for supporting medical equipment in the operating room and wherein the second object is an operating table and wherein the first angle is between approximately 20° and 30° and wherein the second angle is between approximately 40° and 45°.

12. A method as set forth in claim 11 wherein the cup is disposed in the socket in the acetabulum after the cup has been rotated horizontally through the first particular angle and has been rotated vertically through the second particular angle.

13. The method of claim 1, wherein the pole supports a container of intravenous fluid for insertion into the patient during the operation.

\* \* \* \* \*